United States Patent
Lee et al.

(10) Patent No.: US 10,479,213 B2
(45) Date of Patent: Nov. 19, 2019

(54) BATTERY SWELLING SENSING SYSTEM AND METHOD

(71) Applicant: LG CHEM, LTD., Seoul (KR)

(72) Inventors: Jae-Chan Lee, Daejeon (KR); Gyuyeol Lee, Daejeon (KR); Sooryoung Kim, Daejeon (KR)

(73) Assignee: LG CHEM, LTD., Seoul (KR)

(*) Notice: Subject to any disclaimer, the term of this patent is extended or adjusted under 35 U.S.C. 154(b) by 77 days.

(21) Appl. No.: 15/579,730

(22) PCT Filed: Aug. 18, 2016

(86) PCT No.: PCT/KR2016/009091
§ 371 (c)(1),
(2) Date: Dec. 5, 2017

(87) PCT Pub. No.: WO2017/047937
PCT Pub. Date: Mar. 23, 2017

(65) Prior Publication Data
US 2018/0208074 A1   Jul. 26, 2018

(30) Foreign Application Priority Data
Sep. 14, 2015 (KR) .................. 10-2015-0129551

(51) Int. Cl.
*H02J 7/00* (2006.01)
*B60L 11/18* (2006.01)
(Continued)

(52) U.S. Cl.
CPC ....... *B60L 11/1864* (2013.01); *H01M 2/1077* (2013.01); *H02J 7/009* (2013.01); *G01N 33/0004* (2013.01)

(58) Field of Classification Search
CPC .. H02J 7/009; H01M 10/4228; B60L 11/1864
(Continued)

(56) References Cited

U.S. PATENT DOCUMENTS 7,718,286 B2   5/2010 Fujita
9,093,728 B2   7/2015 Alkemade et al.
(Continued)

FOREIGN PATENT DOCUMENTS

EP              2 645 527 A1    10/2013
KR     10-2006-0058737 A         5/2006
(Continued)

OTHER PUBLICATIONS

International Search Report issued in PCT/KR2016/009091 (PCT/ISA/210), dated Nov. 28, 2016.
(Continued)

*Primary Examiner* — Edward Tso
*Assistant Examiner* — Aaron Piggush
(74) *Attorney, Agent, or Firm* — Birch, Stewart, Kolasch & Birch, LLP (57) ABSTRACT

The present invention relates to a system for detecting swelling of a battery, the system including: a plurality of detecting units which is provided at one or more battery modules of a battery pack, respectively, and detects gas branched from a battery cell of the battery module; a control unit which selects the largest detection value among the detection values of the respective detecting units, determines a level of the selected detection value according to a size of the selected detection value, and controls an operation of a peripheral apparatus based on the corresponding level; and a switch unit which is provided in a connection path of the battery pack and an external power source and is turned on and off according to a signal of the control unit.

15 Claims, 5 Drawing Sheets

(51) Int. Cl.
   *H01M 2/10*   (2006.01)
   *G01N 33/00*   (2006.01)
(58) Field of Classification Search
   USPC .................... 320/134, 136, 147, 163; 429/61
   See application file for complete search history.

(56) References Cited

U.S. PATENT DOCUMENTS

| | | |
|---|---|---|
| 9,425,488 B2 | 8/2016 | Seo et al. |
| 2005/0072212 A1* | 4/2005 | Oishi ..................... G01N 27/16 73/23.21 |
| 2012/0121942 A1* | 5/2012 | Kim .................... H01M 2/0426 429/7 |
| 2014/0038006 A1* | 2/2014 | Sturm ................. H01M 6/5083 429/61 |

FOREIGN PATENT DOCUMENTS

| | | |
|---|---|---|
| KR | 10-0670442 B1 | 1/2007 |
| KR | 10-2009-0131573 A | 12/2009 |
| KR | 10-2010-0071722 A | 6/2010 |
| KR | 10-2015-0046661 A | 4/2015 |
| KR | 10-2015-0097077 A | 8/2015 |

OTHER PUBLICATIONS

European Search Report for Appl. No. 16846758.7 dated May 9, 2018.

\* cited by examiner

BATTERY SWELLING SENSING SYSTEM AND METHOD

TECHNICAL FIELD

This application claims priority to and the benefit of Korean Patent Application No. 10-2015-0129551 filed in the Korean Intellectual Property Office on Sep. 14, 2015, the entire contents of which are incorporated herein by reference.

TECHNICAL FIELD

The present invention relates to a system and a method of detecting swelling of a battery, and particularly, to a system and a method of detecting swelling of a battery, in which detecting units are dispersed inside a battery module to detect gas branched from battery cells, a level is given to the largest detection value among the values that exceed a threshold value according to a size of a detection value, and an operation of a battery circuit, an operation speed of a vehicle, and the like are controlled based on the corresponding level, thereby preventing an accident due to a swelling phenomenon of the battery cell.

BACKGROUND ART

A battery has a characteristic in an easy application according to a product group, excellent preservability, a high energy density, and the like. Further, the battery attracts attention as an energy source for improving an environmentally-friendly characteristic and energy efficiency in that a by-product according to the use of energy is not generated, as well as a primary advantage in that it is possible to decrease the use of fossil fuel.

Because of this, the battery is universally applied to a portable device, an electric vehicle (EV), and an energy storage system (ESS), and the like, and serves as a basis in various industries and simultaneously provide convenience to everyday life.

However, the battery may be abnormally driven according to a usage environment, and for example, when a battery is overcharged or a lifetime of the battery is exhausted, a swelling phenomenon and the like of the battery may be caused due to an electrical and chemical action generated inside the battery.

The swelling phenomenon of the battery may lead to an accident, such as ignition and explosion, as well as shortening of the lifetime of the battery and a decrease in capacity of the battery, so that there is a demand for a stable usage of the battery through careful monitoring and an appropriate control.

Accordingly, various research and development related to a detection of a swelling phenomenon of the battery and a protection of the battery has been conducted, and for example, a technology for detecting a change in a volume of a battery cell according to swelling by using a pressure measuring means and blocking a current through the detection has been publicly known.

However, a physical volume expansion of the battery cell is generated only when the swelling of the battery cell considerably progresses, so that it is difficult to detect and respond to the swelling phenomenon of the battery cell at an early stage, and even though a current is blocked, there is a large risk of ignition due to the considerable progress of the swelling.

As another example, a technology of blocking a current by fracturing a member, such as a bus bar and a tap, by expansive force of the battery cell by the swelling phenomenon is also present.

However, it is not easy for the technology to respond to the swelling phenomenon of the battery cell at an early stage, and spark generable during the fracturing of some of the members may act as ignition sources, thereby causing another reason for ignition.

DETAILED DESCRIPTION OF THE INVENTION

Technical Problem

The present invention is conceived to solve the foregoing problems, and an object of the present invention is to provide a system and a method of detecting swelling of a battery, which detect gas branched from a battery cell in real time and determine a level of a detection value, and control a supply of power to a battery module, a current charging quantity, and the like based on the corresponding level, thereby solving a function problem of a battery incurrable due to a swelling phenomenon of the battery cell.

Further, an object of the present invention is to provide a system and a method of detecting swelling of a battery, which appropriately control an operation speed of a vehicle according to a level of a detection value, as well as a control of an operation of a battery circuit, thereby preventing an accident, such as explosion and ignition of the battery and the vehicle, and securing safety of a passenger of the vehicle.

Another object of the present invention is to provide a system and a method of detecting swelling of a battery, which when a battery cell is present in an abnormal environment, control an operation of a peripheral apparatus, such as a air-cooling type fan and a water-cooling type cooling valve, to be stopped, thereby preventing power consumption by unnecessary driving of the peripheral apparatus.

Technical Solution

According to an exemplary embodiment of the present invention, a system for detecting swelling of a battery includes: a plurality of detecting units which is provided at one or more battery modules of a battery pack, respectively, and detects gas branched from a battery cell of the battery module; a control unit which selects the largest detection value among the detection values of the respective detecting units, determines a level of the selected detection value according to a size of the selected detection value, and controls an operation of a peripheral apparatus based on the corresponding level; and a switch unit which is provided in a connection path of the battery pack and an external power source and is turned on and off according to a signal of the control unit.

The detecting units may be dispersed at upper, lower, left, right, front, and rear sides inside the battery module.

Each of the detecting units may include a carbon monoxide detecting sensor, a carbon dioxide detecting sensor, and a methane detecting sensor.

The detecting value may be formed as one set of values including a carbon monoxide detection value, a carbon dioxide detection value, and a methane detection value.

The control unit may compare the detection value of each of the detecting units with a predetermined threshold value, select the largest detection value among the detection values exceeding the threshold values, and determine a level of the selected detection value according to the size of the selected detection value.

The level of the selected detection value may be determined as one of a first level, a second level, and a third level according to the degree of swelling risk.

When the level of the selected detection value is determined as one of the first level, the second level, and the third level, the control unit may transmit a vehicle speed control signal based on the corresponding level to an electronic control unit (ECU) of a vehicle.

When the level of the selected detection value is determined as the third level, the control unit may transmit an off operation signal to the switch unit after a predetermined time elapses.

When the level of the selected detection value is determined as the third level, the control unit may transmit a predetermined alarm signal to a display device pre-installed in a vehicle.

When the level of the selected detection value is determined as the second level, the control unit may control the quantity of charging current flowing into the battery pack from the external power source.

According to another exemplary embodiment of the present invention, a method of detecting swelling of a battery includes: detecting, by a plurality of detecting units provided at one or more battery modules of a battery pack, respectively, gas branched from a battery cell of the battery module; selecting, by a control unit, the largest detection value among the detection values of the respective detecting units, determining a level of the selected detection value according to a size of the selected detection value, and controlling an operation of a peripheral apparatus based on the corresponding level; and being turned on and off, by a switch unit provided in a connection path of the battery pack and an external power source, according to a signal of the control unit.

The detecting units may be dispersed at upper, lower, left, right, front, and rear sides inside the battery module.

Each of the detecting units may include a carbon monoxide detecting sensor, a carbon dioxide detecting sensor, and a methane detecting sensor.

The detecting value may be formed as one set of values including a carbon monoxide detection value, a carbon dioxide detection value, and a methane detection value.

The controlling may include comparing, by the control unit, the detection value of each of the detecting units with a predetermined threshold value, selecting the largest detection value among the detection values exceeding the threshold values, and determining a level of the selected detection value according to the size of the selected detection value.

The level of the selected detection value may be determined as one of a first level, a second level, and a third level according to the degree of swelling risk.

The controlling may include, when the level of the selected detection value is determined as one of the first level, the second level, and the third level, transmitting a vehicle speed control signal based on the corresponding level to an electronic control unit (ECU) of a vehicle.

The controlling may further include, when the level of the selected detection value is determined as the third level, transmitting an off operation signal to the switch unit after a predetermined time elapses.

The controlling may further include, when the level of the selected detection value is determined as the third level, transmitting a predetermined alarm signal to a display device pre-installed in a vehicle.

The controlling may further include, when the level of the selected detection value is determined as the second level, controlling the quantity of charging current flowing into the battery pack from the external power source.

Advantageous Effects

According to one aspect of the present invention, gas branched from a battery cell is detected in real time and a level is determined according to a size of the detected detection value, and an operation of a battery circuit is controlled based on the corresponding level, thereby decreasing danger of an accident incurrable due to a swelling phenomenon and improving efficiency of an operation of a battery while excluding a simple stop of the operation of the battery.

In this case, the plurality of detecting units detecting branched gas is dispersed inside the battery modules, respectively, so that it is possible to improve sensitivity of a detection of gas, and partially replace only a corresponding battery module, in which a swelling phenomenon is incurred, among the plurality of battery modules, thereby promoting convenience of maintenance and repair and decreasing costs.

Further, a speed of an operated vehicle is controlled by using a battery as driving energy according to a level of a detection value, thereby preventing an accident incurrable due to an overspeeding operation and securing safety of a passenger of a vehicle when the swelling of the battery cell is incurred.

Further, when the swelling phenomenon is incurred, a supply of power to a battery pack is stopped and an operation of a peripheral apparatus, such as an air-cooling type fan and a water-cooling type cooling value, is stopped, thereby preventing power consumption by unnecessary driving of the peripheral apparatus.

MODE FOR CARRYING OUT THE INVENTION

The present invention will be described in detail below with reference to the accompanying drawings. Herein, repeated descriptions and the detailed description of a publicly known function and configuration that may make the gist of the present invention unnecessarily ambiguous will be omitted. Exemplary embodiments of the present invention are provided so as to more completely explain the present invention to those skilled in the art. Accordingly, the shape, the size, etc., of elements in the figures may be exaggerated for a more clear explanation.

Throughout the specification, unless explicitly described to the contrary, the word "include/comprise" and variations such as "includes/comprises" or "including/comprising" mean further including other constituent elements, not excluding the other constituent elements.

In addition, the term " . . . unit" described in the specification means a unit for processing at least one function and operation and may be implemented by hardware components or software components and combinations thereof.

Figure 1:
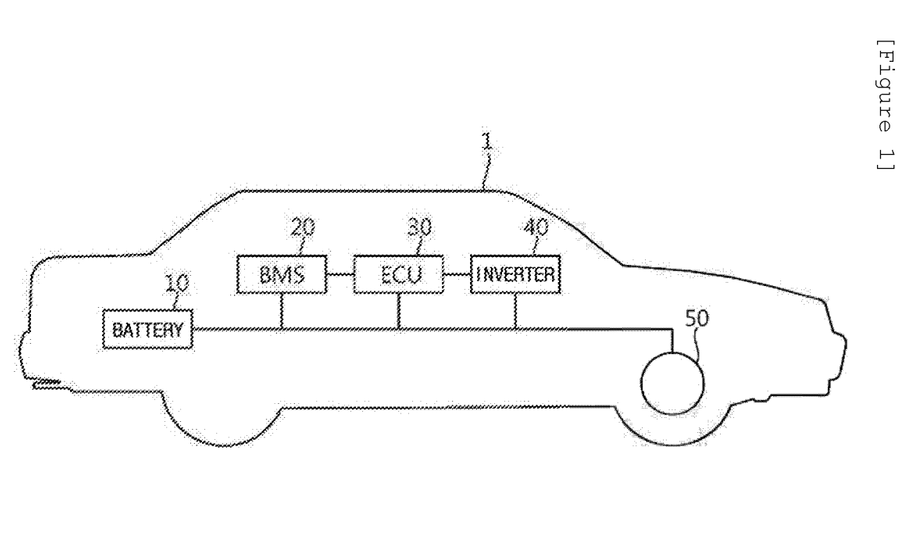
FIG. 1 is a diagram schematically illustrating an electric vehicle, to which a system and a method of detecting swelling of a battery according to an exemplary embodiment of the present invention are applicable.

FIG. 1 is a diagram schematically illustrating an electric vehicle 1, to which a system and a method of detecting swelling of a battery according to an exemplary embodiment of the present invention are applicable.

However, the system and the method of detecting swelling of the battery according to the exemplary embodiment of the present invention are applicable to various technical fields, to which a battery is applied, in addition to the electric vehicle 1.

Referring to FIG. 1, the electric vehicle 1 may include a battery 10, a battery management system (BMS) 20, an electronic control unit (ECU) 30, an inverter 40, and a motor 50.

The battery 10 is an electric energy source providing driving force to the motor 50 and driving the electric vehicle 1, and may be charged or discharged by the inverter 40 according to the driving of the motor 50 and/or an internal combustion engine (not illustrated).

The BMS 20 may estimate a state of the battery 10 and control a charging/discharging current of the battery 10 by using information about the state, and further control an opening/closing operation of a contactor.

The ECU 30 is an electronic control apparatus controlling a state of the electric vehicle 1, and for example, may determine a degree of torque based on information about an accelerator, a break, a speed, and the like, and control an output of the motor to correspond to the torque information.

The inverter 40 may charge or discharge the battery 10 based on a control signal of the ECU 30, and the motor 50 may drive the electric vehicle 1 based on electric energy of the battery 10 and the control information transmitted from the ECU 30.

As described above, in the electric vehicle 1, the battery 10 is a core element providing driving force, and when the battery 10 is in an abnormal state, this may cause a failure of the electric vehicle 1 and various accidents.

For example, when the battery 10 is present in an environment, such as overcharging and a short-circuit, or a lifetime of the battery 10 is completely exhausted, gas is generated inside the battery 10 due to an electrical and chemical reaction to increase internal pressure of the battery 10, and this may lead to a swelling phenomenon of the battery 10 which may cause an accident, such as an explosion and ignition.

Accordingly, the monitoring of a state of the battery 10 and an appropriate protection of the battery 10 according to a situation are the important matters for stably operating the battery 10 and are preparations for preventing various accidents due to abnormal driving of the battery 10 and securing safety of a passenger, and hereinafter, the system and the method of detecting swelling of the battery according to the exemplary embodiment of the present invention will be described with reference to FIGS. 2 to 5.

Figure 2:
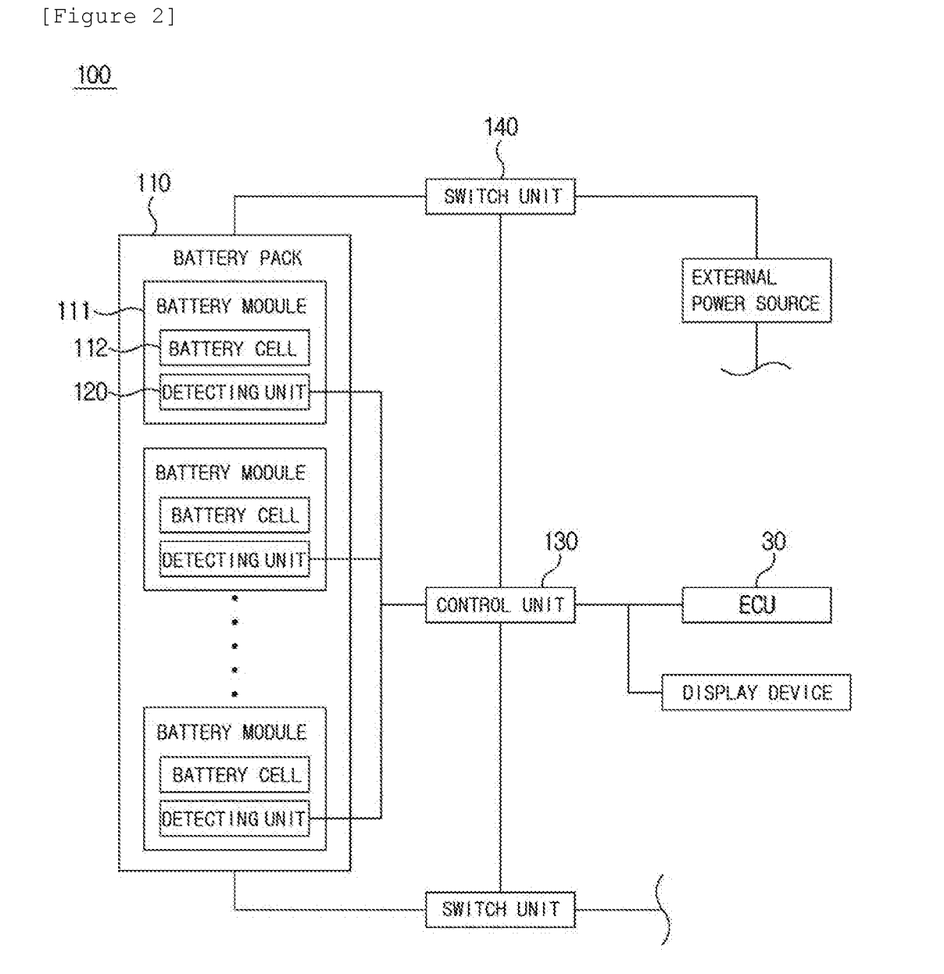
FIG. 2 is a diagram schematically illustrating a circuit diagram of the system for detecting swelling of the battery according to the exemplary embodiment of the present invention.

FIG. 2 is a diagram schematically illustrating a circuit diagram of the system 100 for detecting swelling of the battery according to the exemplary embodiment of the present invention.

Referring to FIG. 2, the system 100 for detecting swelling of the battery according to the exemplary embodiment of the present invention may include a plurality of detecting units 120, a control unit 130, and a switch unit 140.

However, the system 100 for detecting the swelling of the battery illustrated in FIG. 2 is an exemplary embodiment, and constituent elements thereof are not limited to the exemplary embodiment illustrated in FIG. 2, and it is noted that some constituent elements may be added, changed, or removed as necessary.

Further, the battery which is described below is a concept including one or more battery packs 110, and it is noted that each of the battery packs 110 also includes one or more battery modules 111, and similarly, each of the battery modules 111 includes one or more battery cells 112.

First, when a swelling phenomenon is incurred in a predetermined battery cell 112 among the one or more battery cells 112, the detecting unit 120 may detect branched gas.

Figure 3:
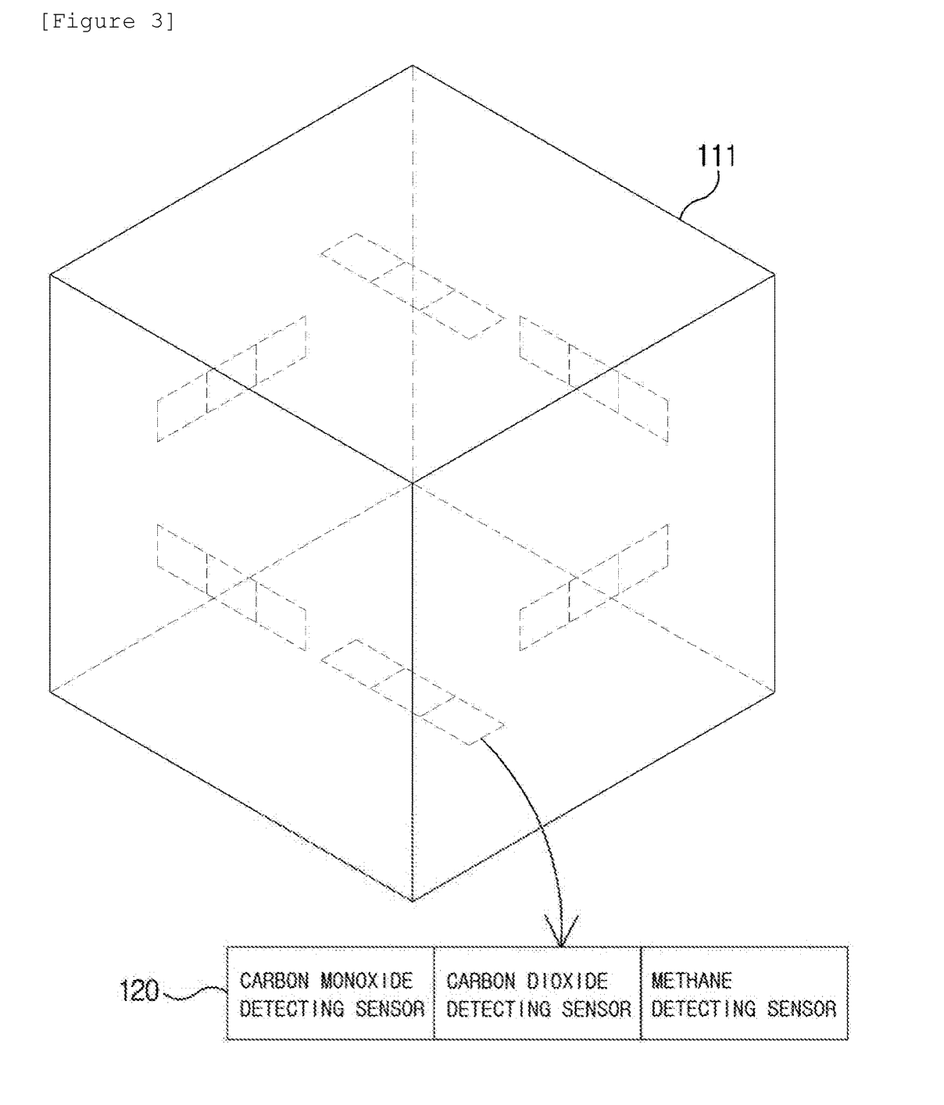
FIG. 3 is a diagram schematically illustrating the case where detecting units of the system for detecting swelling of the battery are provided inside a battery module according to the exemplary embodiment of the present invention.

In this case, the plurality of detecting units 120 may be dispersed at upper, lower, left, right, front, and rear sides inside the battery module 111 as illustrated in FIG. 3, and the plurality of detecting units 120 is dispersed for the purpose of preventing a detection error generable when the single detecting unit 120 is provided, and simultaneously improving sensitivity of the detection of gas.

Typically, when a swelling phenomenon is incurred in the battery cell, main ingredients of the branched gas are carbon monoxide, carbon dioxide, methane, and the like, so that each of the detecting units 120 may include a carbon monoxide detecting sensor, a carbon dioxide detecting sensor, and a methane detecting sensor based on the main ingredients of the branched gas.

Accordingly, detection values measured by the detecting units 120, respectively, may be formed as one set of values including a carbon monoxide detection value, a carbon dioxide detection value, and a methane detection value, and each set of the detection values may be provided to the control unit 130 which is to be described below through an electrical or communicational route.

The control unit 130 may receive the detection values, particularly, the sets of detection values including the carbon monoxide detection value, the carbon dioxide detection value, and the methane detection value, from the detecting units 120, and select a specific detection value set and determine a level of the detection value. Further, the control unit 130 may also control an operation of the peripheral apparatus based on the level of the selected detection value.

In this case, the level of the selected detection value may be determined with one of the plurality of level set with differential ranges based on a degree of swelling risk of the battery cell 112, and for example, the plurality of levels may include a first level, in which the degree of swelling is an alert level, a second level, in which the degree of swelling of the battery cell 112 is a danger level, and a third level, in which the degree of swelling is a serious level.

The control unit 130 may be implemented with the BMS 20 (see FIG. 1) itself, or may be implemented while being included in the BMS, and an algorithm for performing an operation of the control unit 130 may be set in the control unit 130.

The performance of the operation of the control unit 130 will be described in more detail with reference to FIG. 4.

Figure 4:
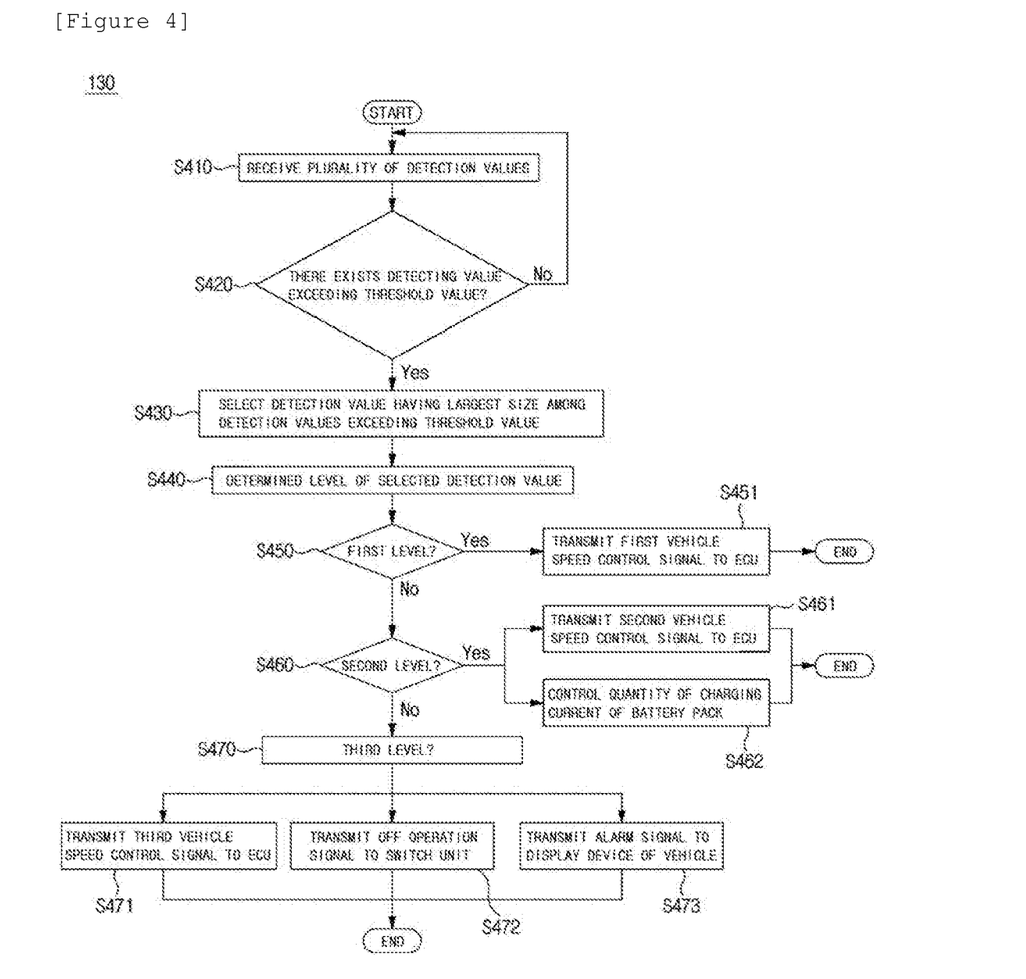
FIG. 4 is a diagram schematically illustrating an algorithm performed in a control unit of the system for detecting swelling of the battery according to the exemplary embodiment of the present invention.

FIG. 4 is a diagram schematically illustrating an algorithm performed in the control unit.

Reviewing each operation of the algorithm, first, the control unit may receive a detection value from each detecting unit (S410), and compare the received detection value with a predetermined threshold value.

Here, the threshold value is a threshold value for the quantity of gas branched when the swelling phenomenon is incurred in the battery cell, and may be formed of a set including a carbon monoxide threshold value, a carbon dioxide threshold value, and a methane threshold value, and may be set by a user.

That is, in the comparison operation, a carbon monoxide detection value is compared with a carbon monoxide threshold value, a carbon dioxide detection value is compared with a carbon dioxide threshold value, and similarly, a methane detection value is compared with a methane threshold value, and only when all of the carbon monoxide detection value, the carbon dioxide detection value, and the methane threshold value exceed the corresponding threshold values, it may be determined that the detection value (set) exceeds the threshold value (set) (S420).

When the number of detection values exceeding the threshold value is two or more, the largest detection value among the plurality of detection values is selected (S430), and herein, the size may refer to an average of the carbon monoxide detection value, the carbon dioxide detection value, and the methane detection value.

Sequentially, a level of the selected detection value may be determined based on a first level, a second level, and a third level which are predetermined with differential ranges. That is, when the size of the selected detection value is included in an alert range, a level of the selected detection value may be determined as the first level, when the size of the selected detection value is included in a danger range, a level of the selected detection value may be determined as the second level, and when the size of the selected detection value is included in a serious range, a level of the selected detection value may be determined as the third level.

When the level of the selected detection value is determined as the first level (S450), the control unit may transmit a vehicle speed (for example, 80 km or less) control signal corresponding to the first level to the ECU of the vehicle (S451).

In this case, the signal may be transmitted by using controller area network (CAN) communication, but the present invention is not limited thereto, and various schemes of communication, such as ZigBee communication, WiFi, radio frequency (RF) communication, and Bluetooth low energy (BLE) communication, may be applied.

Even when the level of the selected detection value is determined as the second level (S460), the control unit may transmit a vehicle speed (for example, 50 km or less) control signal corresponding to the second level to the ECU of the vehicle (S461).

Further, the quantity of charging current flowing into a battery pack from an external power source may also be controlled by controlling a variable resistor (not illustrated) provided in a connection path of the battery pack and the external power source. The configuration may aim to prevent overcharging of the battery pack and minimize the quantity of gas branched from the battery cell.

Last, when the level of the selected detection value is determined as the third level (S470), the control unit may similarly transmit a vehicle speed (for example, 10 km or less) control signal corresponding to the third level to the ECU of the vehicle (S471), and may transmit an alarm signal to a display device, such as a navigation device and a monitor for a vehicle (S473).

In this case, the alarm may be audio-visually formed, such as a predetermined alarm sound and an alarm message, and may enable a passenger of the vehicle to recognize the incurrence of a swelling phenomenon of the battery cell.

Particularly, when the level of the selected detection value is determined as the third level, after a predetermined time elapses, the control unit may transmit an off operation signal to a switch unit 140 (see FIG. 1) provided in the connection path of the battery pack and the external power source.

Herein, the switch unit may be formed of one or more of a field effect transistor and a relay, and the kind of contactor forming the switch unit is not limited, but may be various.

Further, the predetermined time is a concept securing a minimum vehicle operation, and may be, for example, a time consumed for travelling about 10 km, and sudden blocking of the connection between the battery pack and the external power source may cause an accident in the case of an electric vehicle, so that the configuration may consider such a situation.

Further, the control unit may transmit the off operation signal to the switch unit and simultaneously control an operation of a peripheral apparatus, such as an air-cooling type fan and a water-cooling type cooling value, to be stopped, so that it is possible to prevent power consumption according to unnecessary driving of the peripheral apparatus.

As described above, the control unit 130 may determine a level of the largest detection value among the detection values exceeding the threshold value through the predetermined algorithm, and control an operation of a battery circuit and an operation of the peripheral apparatus based on the corresponding level.

Figure 5:
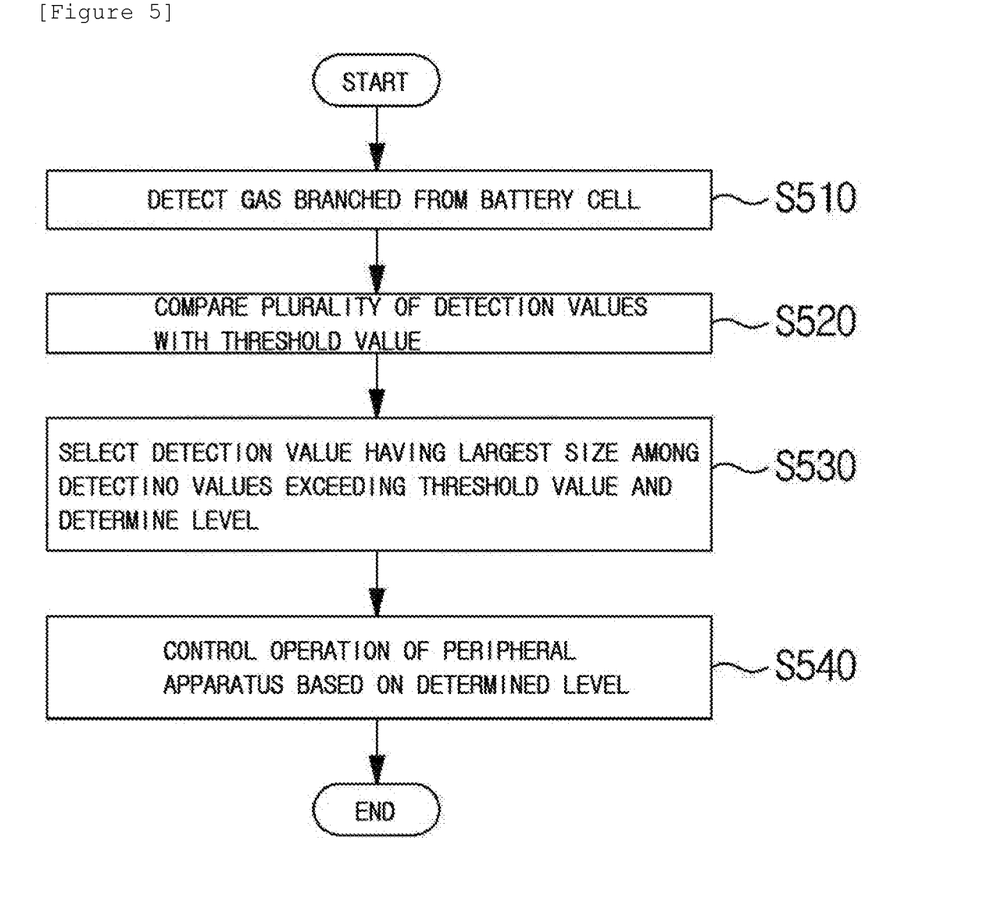
FIG. 5 is a flowchart illustrating the method of detecting swelling of the battery according to the exemplary embodiment of the present invention.

FIG. 5 is a flowchart illustrating the method of detecting swelling of the battery according to the exemplary embodiment of the present invention.

When the method of detecting swelling of the battery according to the exemplary embodiment of the present invention starts, each of the plurality of detecting units dispersed inside the battery modules detects gas branched from the battery cell, and provides a result of the detection to the control unit (S510).

The control unit compares each of the detection values with a threshold value, and determines whether there is the detection value exceeding the threshold value (S520). When the number of detection values exceeding the threshold value is two or more, the control unit selects the largest detection value, and determines a level of the selected detection value according to the size of the selected detection value (S530).

Then, the control unit controls an operation speed of the vehicle, controls the quantity of charging current flowing into the battery pack, controls an operation of the battery circuit, such as a control of an off operation of the switch unit, and controls an operation of the peripheral apparatus based on the level of the selected detection value (S540).

In the forgoing, the specific exemplary embodiment of the present invention has been illustrated and described, but it is apparent to those skilled in the art that the technical spirit of the present invention is not limited by the accompanying drawings and the described contents, and may be modified in various forms without departing from the spirit of the present invention, and the modifications are considered to belong to the claims of the present invention without departing from the spirit of the present invention.

The invention claimed is:

1. A system for detecting swelling of a battery, the system comprising:
   a plurality of detecting units which is provided at one or more battery modules of a battery pack, respectively, and detects gas branched from a battery cell of the battery module;
   a control unit which selects the largest detection value among the detection values of the respective detecting units, determines a level of the selected detection value according to a size of the selected detection value, and controls an operation of a peripheral apparatus based on the corresponding level; and
   a switch unit which is provided in a connection path of the battery pack and an external power source and is turned on and off according to a signal of the control unit,
   wherein the control unit compares the detection value of each of the detecting units with a predetermined threshold value, selects the largest detection value among the detection values exceeding the threshold values, and determines a level of the selected detection value according to the size of the selected detection value,
   wherein the level of the selected detection value is determined as one of a first level, a second level, and a third level according to the degree of swelling risk, and
   wherein when the level of the selected detection value is determined as one of the first level, the second level, and the third level, the control unit transmits a vehicle speed control signal based on the corresponding level to an electronic control unit (ECU) of a vehicle.

2. The system of claim 1, wherein the detecting units are dispersed at upper, lower, left, right, front, and rear sides inside the battery module.

3. The system of claim 1, wherein each of the detecting units includes a carbon monoxide detecting sensor, a carbon dioxide detecting sensor, and a methane detecting sensor, and
   the detecting value is formed as one set of values including a carbon monoxide detection value, a carbon dioxide detection value, and a methane detection value.

4. The system of claim 1, wherein when the level of the selected detection value is determined as the third level, the control unit transmits an off operation signal to the switch unit after a predetermined time elapses.

5. The system of claim 1, wherein when the level of the selected detection value is determined as the third level, the control unit transmits a predetermined alarm signal to a display device pre-installed in a vehicle.

6. The system of claim 1, wherein when the level of the selected detection value is determined as the second level, the control unit controls the quantity of charging current flowing into the battery pack from the external power source.

7. A method of detecting swelling of a battery, the method comprising:
   detecting, by a plurality of detecting units provided at one or more battery modules of a battery pack, respectively, gas branched from a battery cell of the battery module;
   selecting, by a control unit, the largest detection value among the detection values of the respective detecting units, determining a level of the selected detection value according to a size of the selected detection value, and controlling an operation of a peripheral apparatus based on the corresponding level; and
   being turned on and off, by a switch unit provided in a connection path of the battery pack and an external power source, according to a signal of the control unit,
   wherein the controlling includes comparing, by the control unit, the detection value of each of the detecting units with a predetermined threshold value, selecting the largest detection value among the detection values exceeding the threshold values, and determining a level of the selected detection value according to the size of the selected detection value,
   wherein the level of the selected detection value is determined as one of a first level, a second level, and a third level according to the degree of swelling risk, and
   wherein the controlling includes, when the level of the selected detection value is determined as one of the first level, the second level, and the third level, transmitting a vehicle speed control signal based on the corresponding level to an electronic control unit (ECU) of a vehicle.

8. The method of claim 7, wherein the detecting units are dispersed at upper, lower, left, right, front, and rear sides inside the battery module.

9. The method of claim 7, wherein each of the detecting units includes a carbon monoxide detecting sensor, a carbon dioxide detecting sensor, and a methane detecting sensor, and
   the detecting value is formed as one set of values including a carbon monoxide detection value, a carbon dioxide detection value, and a methane detection value.

10. The method of claim 7, wherein the controlling further includes, when the level of the selected detection value is determined as the third level, transmitting an off operation signal to the switch unit after a predetermined time elapses.

11. The method of claim 7, wherein the controlling further includes, when the level of the selected detection value is determined as the third level, transmitting a predetermined alarm signal to a display device pre-installed in a vehicle.

12. The method of claim 7, wherein the controlling further includes, when the level of the selected detection value is determined as the second level, controlling the quantity of charging current flowing into the battery pack from the external power source.

13. A system for detecting swelling of a battery, the system comprising:
   a plurality of detecting units which is provided at one or more battery modules of a battery pack, respectively, and detects gas branched from a battery cell of the battery module;
   a control unit which selects the largest detection value among the detection values of the respective detecting units, determines a level of the selected detection value according to a size of the selected detection value, and controls an operation of a peripheral apparatus based on the corresponding level; and
   a switch unit which is provided in a connection path of the battery pack and an external power source and is turned on and off according to a signal of the control unit,
   wherein the control unit compares the detection value of each of the detecting units with a predetermined threshold value, selects the largest detection value among the detection values exceeding the threshold values, and determines a level of the selected detection value according to the size of the selected detection value, and
   wherein the level of the selected detection value is determined according to the degree of swelling risk, and the control unit transmits a vehicle speed control signal based on the corresponding level to an electronic control unit (ECU) of a vehicle.

14. The system of claim 13, wherein the detecting units are dispersed at upper, lower, left, right, front, and rear sides inside the battery module.

15. The system of claim 13, wherein each of the detecting units includes a carbon monoxide detecting sensor, a carbon dioxide detecting sensor, and a methane detecting sensor, and the detecting value is formed as one set of values including a carbon monoxide detection value, a carbon dioxide detection value, and a methane detection value.

\* \* \* \* \*